US008686064B2

(12) United States Patent
Shimp et al.

(10) Patent No.: US 8,686,064 B2
(45) Date of Patent: Apr. 1, 2014

(54) COUPLING AGENTS FOR ORTHOPEDIC BIOMATERIALS

(75) Inventors: Lawrence A. Shimp, Morganville, NJ (US); David Knaack, Summit, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 647 days.

(21) Appl. No.: 11/856,977

(22) Filed: Sep. 18, 2007

(65) Prior Publication Data

US 2008/0009955 A1 Jan. 10, 2008

Related U.S. Application Data

(62) Division of application No. 10/681,651, filed on Oct. 8, 2003, now Pat. No. 7,270,813.

(60) Provisional application No. 60/416,904, filed on Oct. 8, 2002.

(51) Int. Cl.
*A61F 2/28* (2006.01)
*A61K 35/32* (2006.01)
*A61F 2/02* (2006.01)

(52) U.S. Cl.
USPC ........... 523/116; 523/113; 523/115; 424/423; 424/549; 623/23.61; 623/23.63

(58) Field of Classification Search
USPC ............ 523/116, 113, 115; 623/23.61, 23.63; 424/423, 549
See application file for complete search history.

(56) References Cited

U.S. PATENT DOCUMENTS

| | | | |
|---|---|---|---|
| 3,892,649 A | 7/1975 | Phillips et al. | |
| 3,949,073 A | 4/1976 | Daniels et al. | |
| 4,172,128 A * | 10/1979 | Thiele et al. | 424/549 |
| 4,183,874 A | 1/1980 | Fan et al. | |
| 4,187,852 A | 2/1980 | Urry et al. | |
| 4,192,021 A | 3/1980 | Deibig et al. | |
| 4,263,185 A | 4/1981 | Belykh et al. | |
| 4,314,380 A | 2/1982 | Miyata et al. | |
| 4,394,370 A | 7/1983 | Jefferies | |
| 4,440,750 A | 4/1984 | Glowacki et al. | |
| 4,516,276 A | 5/1985 | Mittelmeier et al. | |
| 4,551,156 A | 11/1985 | Li | |
| 4,645,503 A | 2/1987 | Lin et al. | |
| 4,776,890 A | 10/1988 | Chu | |
| 4,778,834 A * | 10/1988 | Murray | 523/212 |
| 4,783,504 A | 11/1988 | St. Clair et al. | |
| 4,863,732 A | 9/1989 | Nathan et al. | |
| 4,882,149 A | 11/1989 | Spector | |
| 5,073,114 A | 12/1991 | Detsch | |
| 5,162,445 A | 11/1992 | Powers et al. | |
| 5,246,782 A | 9/1993 | Kennedy et al. | |
| 5,262,461 A | 11/1993 | Serizawa et al. | |
| 5,324,519 A | 6/1994 | Dunn et al. | |
| 5,333,626 A | 8/1994 | Morse et al. | |
| 5,338,772 A | 8/1994 | Bauer et al. | |
| 5,417,975 A | 5/1995 | Lussi et al. | |
| 5,468,544 A | 11/1995 | Marcolongo et al. | |
| 5,507,813 A | 4/1996 | Dowd et al. | |
| 5,513,662 A | 5/1996 | Morse et al. | |
| 5,531,791 A | 7/1996 | Wolfinbarger, Jr. | |
| 5,573,771 A | 11/1996 | Geistlich et al. | |
| 5,573,971 A | 11/1996 | Cleeves | |
| 5,606,000 A | 2/1997 | Jadhav et al. | |
| 5,607,269 A | 3/1997 | Dowd et al. | |
| 5,626,861 A | 5/1997 | Laurencin et al. | |
| 5,676,146 A | 10/1997 | Scarborough | |
| 5,681,872 A * | 10/1997 | Erbe | 523/114 |
| 5,736,372 A | 4/1998 | Vacanti et al. | |
| 5,766,618 A | 6/1998 | Laurencin et al. | |
| 5,846,484 A | 12/1998 | Scarborough et al. | |
| 5,899,939 A | 5/1999 | Boyce et al. | |
| 5,948,386 A | 9/1999 | Katti et al. | |
| 6,027,744 A | 2/2000 | Vacanti et al. | |
| 6,033,582 A | 3/2000 | Lee et al. | |
| 6,119,028 A | 9/2000 | Schulman et al. | |
| 6,123,731 A * | 9/2000 | Boyce et al. | 623/23.63 |
| 6,165,486 A | 12/2000 | Marra et al. | |
| 6,201,039 B1 | 3/2001 | Brown et al. | |
| 6,217,614 B1 | 4/2001 | Fages et al. | |
| 6,261,586 B1 | 7/2001 | McKay | |
| 6,294,041 B1 * | 9/2001 | Boyce et al. | 156/275.5 |
| 6,294,187 B1 | 9/2001 | Boyce et al. | |
| 6,352,667 B1 | 3/2002 | English | |
| 6,395,036 B1 | 5/2002 | Czernuszka et al. | |
| 6,399,693 B1 | 6/2002 | Brennan et al. | |

(Continued)

FOREIGN PATENT DOCUMENTS

| | | | |
|---|---|---|---|
| WO | WO 98/19718 | 5/1998 | |
| WO | WO 9920692 A1 * | 4/1999 | ............ C08L 51/00 |

OTHER PUBLICATIONS

Aspenberg, et al., *Thirty Ninth Annual Meeting, Orthapedic Research Society*, 18:101, 1993.
Baker, Gregory L., http://www.cem.msu.edu/~gradoff/brochf/Baker.htm, printed Aug. 2002.
Ballock, et al., *Thirty Ninth Meeting Annual Meeting, Orthopedic Research Society*, 18:734, 1993.
Boesch, P., "Bone Grafting with Fibrin Glue", *Wiener Klinische Wochenschroft Supplementum*, 93, No. 124, pp. 3-26, 1981.
Bonar, et al., *J. Bone Min. Res.*, 6:1167-1176, 1991.
Cook, et al., *Thirty Ninth Annual Meeting, Orthapedic Research Society*, 18:484, 1993.
Dandurand, et al., *J. Biomed. Mater. Res.*, 24:1377-1384, 1990.
Delpech, et al., *Clin. Mater.*, 5:209-216, 1990.
Dupraz, et al., *J. Biomed. Mater. Res.*, 30:231-238, 1996.
Glowacki, et al., *J. Cellular Biochem.*, 45:292-302, 1991.

(Continued)

*Primary Examiner* — Michael Pepitone
(74) *Attorney, Agent, or Firm* — Sorell Lenna & Schmidt LLP

(57) ABSTRACT

The invention provides a method for the preparation of bone-polymer composites wherein the mineral portion of the bone is treated with a coupling agent before being incorporated into a biocompatible polymeric matrix. The resulting composites may be used as such or be further processed to form an osteoimplant.

27 Claims, No Drawings

(56) References Cited

U.S. PATENT DOCUMENTS

| | | | |
|---|---|---|---|
| 6,406,498 | B1 | 6/2002 | Törmälä et al. |
| 6,432,436 | B1 | 8/2002 | Gertzman et al. |
| 6,478,825 | B1 * | 11/2002 | Winterbottom et al. ... 623/23.63 |
| 2001/0014831 | A1 * | 8/2001 | Scarborough ............. 623/23.51 |
| 2001/0043940 | A1 * | 11/2001 | Boyce et al. ............. 424/423 |
| 2002/0035401 | A1 * | 3/2002 | Boyce et al. ............. 623/23.51 |
| 2002/0098222 | A1 | 7/2002 | Wironen et al. |
| 2003/0171451 | A1 * | 9/2003 | White et al. ............. 523/117 |
| 2005/0251267 | A1 | 11/2005 | Winterbottom et al. |

OTHER PUBLICATIONS

Han, et al., "Synergistic Effects of Lecithin and Human DBM on Bone Induction in Nude Rats", *Society for Biomaterials*, 28th Annual Meeting Transactions, 2002 (abstract).

Hooper, et al., *J. Bioactive and Compatible Polymers*, 10:327-340, 1995.

Hunt, et al., *Thirty Ninth Annual Meeting, Orthapedic Research Society*, 18:489, 1993.

Hurley, et al., *Milit. Med.*, 101-104, 1957.

International Search Report, PCT/US03/31990, mailed on Mar. 31, 2004.

Iwasaki, et al., *Thirty Ninth Annual Meeting, Orthapedic Research Society*, 18:483, 1993.

Kershaw, *Pharm. J.*, 8:537, 1963.

Liu, et al., *J. Biomed. Mater. Res.*, 40:257-263, 1998.

Liu, et al., *J. Mater. Sci. Mater. Med.*, 9:23-30, 1998.

Misra, et al., *J. Dent. Res.*, 12:1405-1408, 1985.

Miyamoto, et al., *Thirty Ninth Annual Meeting, Orthapedic Research Society*, 18:99, 1993.

Nazhat, S.N., et al., "Dynamic Mechanical Behaviour of Modified Hydroxyapatite Reinforced Polyethylene Composites", *Fifth World Biomaterials Congress*, p. 83, May 29-Jun. 2, 1996.

Nishizawa, et al., *Chem. Soc. Jpn.*, 1:63-67, 1995.

Pulapura, et al., *Biopolymers*, 32:411-417, 1992.

Reis, et al., *Adv. Polym. Tech.*, 16:263-277, 1997.

Ripamonti, et al., *CRC Critical Reviews in Oral Biol. Med.*, 3:1-14, 1992.

Ripamonti, et al., *J. Plastic and Reconstructive Surg.*, 89:731-739, 1991.

Ripamonti, et al., *Matrix*, 11:404-411, 1991.

Ripamonti, et al., *Matrix*, 12:202-212, 1992.

Silane Coupling Agent, http://www.apr.co.kr/silaneen.htm, printed Aug. 7, 2002.

Simmons, D.M., et al., "Evaluation of collagen cross-linking techniques for the stabilization of tissue matrices", *Biotechnol. Appl. Biochem.* 17, 23-29 (1993) (abstract only).

Tangpasuthadol, Varawut, "Thermo-Mechanical Properties and Hydrolytic Degradation of Tyrosine-Derived Polymers for Use in Biomedical Applications", Ph.D. Dissertation, Rutgers, The State University of New Jersey, (Jan. 1999).

Whittaker, et al., "Matrix Metalloproteinases and their Inhibitors—Current Status and Future Challenges", *Celltransmissions*, 17, prior to Jun. 13, 2002.

Yasko, et al., *Thirty Ninth Annual Meeting, Orthopedic Research Society*, 18:100, 1993.

Zhiyuan Zhong, et al., "Calcium methoxide initiated ring-opening polymerization of ε-caprolactone and L-lactide", *Polymer Bulletin* 46, 51-57 (2001).

Dumas et al., "Synthesis and Characterization of an Injectable Allograft Bone/Polymer Composite Bone Void Filler with Tunable Mechanical Properties" Tissue Engineering, 16:2505-2518 (2010).

* cited by examiner

COUPLING AGENTS FOR ORTHOPEDIC BIOMATERIALS

This application is a divisional of and claims priority under 35 U.S.C. 120 to application, U.S. Ser. No. 10/681,651, filed Oct. 8, 2003, now U.S. Pat. No. 7,270,813; which claims priority under 35 U.S.C. 119(e) to provisional application, U.S. Ser. No. 60/416,904, filed Oct. 8, 2002, the entire contents of each of which are incorporated by reference herein.

BACKGROUND OF THE INVENTION

The importance of orthopedic substitutes is underscored by the fact that the World Health Authority has decreed 2000-2010 the Bone and Joint Decade. Bone substitutes are the most common implanted materials, and are second only to transfused blood products as products delivered internally. Bone substitutes are used to help repair or replace skeletal deficiencies resulting from trauma, tumors, surgery, congenital and degenerative diseases or abnormal development.

Current methods for the repair of bony defects include autografting and allografting. Autologous bone grafts utilize cortical and cancellous bone that is harvested and transplanted within the same patient. Autologous bone grafting is currently the most effective procedure for repair of bony defects, and is the standard against which all other methods are judged. The advantages of autologous bone grafts include their excellent success rate, low risk of transmitting disease, and histocompatibility. Allografts utilize bone harvested from a different organism of the same species, and lack the osteogenic properties of autografts. Their healing capacity is consequently lower. Allografting also carries a risk of transmitting certain diseases, and may elicit intense immunological reactions. Although both autologous and allogenic grafts can be used successfully, they suffer from problems associated with harvesting costs, limited availability, and donor site morbidity.

Purified and synthetic materials, including metals, plastics, ceramics, and collagen-based matrices have been developed as bone substitutes in an attempt to obviate these problems. These materials can be produced in large quantities and in a variety of shapes and sizes, and most are non-immunogenic. However, metals and plastics, which were the first synthetic materials to be used clinically, are subject to fatigue, fracture, and wear, and do not remodel or resorb with time. More recently, the FDA has approved a coral derived hydroxyapatite for use in contained bone defects, and a purified collagen/ceramic composite material for use in acute long bone fractures. Although these materials avoid the morbidity involved in harvesting bone and eliminate the problems associated with limited donor bone availability, they are much less effective than autografts. This explains, at least partly, the fact that in 2000 synthetic bone substitutes represented less than 15% of the global use of bone grafts.

There is, therefore, a continued interest in the development of new, improved bone graft materials. Knowledge of the structure and mechanical properties of bone and a better understanding of the natural bone healing process have allowed investigators to define desirable characteristics of a successful implant material. Bone substitutes should desirably be biocompatible, osteoconductive, integrative and mechanically compatible with native bone. Materials that are osteoinductive are particularly desirable. These materials should provide cell anchorage sites, mechanical stability and structural guidance, and serve as a source of osteogenesis over the time period required for bone replacement.

Since the biological and mechanical properties of bone result from its microstructural features, a strategy in the development of the ideal substitute material is to mimic the structure of natural bone. Bone is a composite material made up of organic and inorganic components, where the inorganic or mineral phase represents 60-70% of the total dry bone weight. The organic phase is a viscous gel-like material comprised primarily of type I collagen while the mineral component consists of a crystalline form of calcium phosphate containing carbonate ions, small amounts of sodium, magnesium, hydrogenophosphate ions and other trace elements. The interaction of the hard brittle mineral phase and the flexible organic matrix gives bone its unique mechanical properties. The ability of bone to perpetually remodel is ascribed, at least in part, to the calcium phosphate ratio of the mineral phase as well as to the particular crystalline nature of bone. A sound approach in developing a bone substitute is therefore to combine minerals to an organic polymeric matrix to generate a composite material exhibiting the toughness and flexibility of the polymer and the strength and hardness of the mineral filler.

In recent years, several of these composites have been designed and developed, with powders or ceramics of calcium phosphate (the main bone mineral component) acting as inorganic fillers. Among the calcium phosphate ceramics, hydroxyapatite and tricalcium phosphate ceramics are the most commonly used. Calcium phosphate-based composites possess unique advantages over their constituents, combining the osteoconductivity of the mineral with the easy processing of polymers. In addition, by taking advantage of the wide range of properties of polymers, composites can be made to meet the needs of a large variety of clinical applications. Numerous patents disclose the preparation and composition of such bone substitutes made of calcium phosphate and natural (U.S. Pat. Nos. 4,516,276; 4,776,890; 5,626,861; 6,201,039; and 6,395,036) or synthetic (U.S. Pat. Nos. 4,192,021; 4,263,185; 4,187,852; and 5,338,772) polymers.

Another series of composites, based on the use of bone particles as mineral fillers, has also been developed. Most of these composite materials are prepared from demineralized bone (from human or animal origin) and biocompatible polymers (see, for example, U.S. Pat. Nos. 4,394,370; 4,440,750; 4,863,732; and 5,531,791). The demineralization process is carried out to totally or partially remove minerals and better expose the bone collagen in order to favor the binding of the bone particles to the organic polymer matrix. The resulting compositions can be delivered in a fluid or gel state, they promote cellular infiltration from adjacent osseous tissues, and may possess osteoinductive and osteoconductive properties. Implantable sponges, bandages or prostheses have been formed from these demineralized bone/collagen composites (U.S. Pat. No. 4,394,370).

However, demineralized materials are rarely employed as load-bearing bone products, which are used at implant sites where the bone graft is expected to withstand some level of physical load. Several attempts have been made to produce materials with mechanical properties as close as possible to those of natural bone. Some preparation methods disclose removing all organic material from bone to yield bone mineral by pyrolytic or chemical processes (U.S. Pat. No. 4,882,149) or by using a fluid in the supercritical state (U.S. Pat. No. 6,217,614). Other procedures advocate the removal of only part of the organic component (in U.S. Pat. No. 6,261,586, for example, the bone material is processed to remove associated non-collagenous bone proteins but naturally associated native collagen materials and bone minerals are preserved). Composites have been formed by combination of these nondemineralized bone materials with natural polymers, such as collagen and gelatin (U.S. Pat. Nos. 4,314,380 and 5,573,771) and synthetic polymers, such as lactic polyester (U.S. Pat. No. 5,573,771). Most of these products are intended to be used as remodeling implants, vertebral spacers or prosthetic bone replacements.

Although the composite materials described above have led to the production of biocompatible load-bearing implants with attractive characteristics, they are still in need of improvement. Actually, none of the calcium phosphate-based composites have been shown to possess in vivo mechanical properties comparable to those of natural bone and in most cases, the same is true for the bone-composite materials. In general, these composites exhibit a poor polymer/filler interface [Reis et al. "Structure development and control of injection-moulded hydroxyapatite-reinforced starch/EVOH composites" Adv. Polym. Tech. 16:263-277 (1997)]. In the absence of a good interfacial adhesion between the organic polymer and the mineral filler, transfer of the stresses experienced by the load-bearing implant from the "soft" polymer to the "hard" filler is difficult. A lack of adhesion between the two phases results in early failure. In the case of industrial composites, the compatibility between the filler and the polymer has long been known to improve by using several types of surface coatings, coupling agents, or other additives.

In the field of biomaterials, similar methods have recently been applied to improve the interface of hydroxyapatite/polymer composites using coupling agents [Nishizawa et al. "Surface modification of calcium phosphate ceramics with silane coupling agents" Chem. Soc. Jpn. 1:63-67 (1995); Dupraz et al. "Characterization of silane-treated hydroxyapatite powders for use as filler in biodegradable composites" J. Biomed. Mater. Res. 30:231-238 (1996)]; zirconium salts [Misra, "Adsorption of zirconium salts and their acids in hydroxyapatite: The use of salts as coupling agents to dental polymer composites" J. Dent. Res. 12:1405-1408 (1985)]; and polyacids [Liu et al. "Surface modification of hydroxyapatite to introduce interfacial bonding with Polyactive™ 70/30 in a biodegradable composite" J. Mater. Sci. Mater. Med. 7:551-557 (1996); and Liu et al. "Polyacids as bonding agents in hydroxyapatite/polyester-ether Polyactive™ 30/70 composites" J. Mater. Sci. Mater. Med. 9:23-30 (1998)]. For the same purpose, hydroxyethyl methacrylate has been chemically coupled to octocalcium phosphate [Delpech et al. "Calcium phosphate and interfaces in orthopedic cements" Clin. Mater. 5:209-216 (1990); and Dandurand et al. "Study of the mineral-organic linkage in an apatitic-reinforced bone cement" J. Biomed. Mater. Res. 24:1377-1384 (1990)], and polyethylene glycol has been grafted to the surface of nano-apatite [Liu et al. "Covalent bonding of PMMA, PBMA, and poly (HEMA) to hydroxyapatite particles" J. Biomed. Mater. Res. 40: 257-263 (1998)]. U.S. Pat. No. 6,399,693 discloses a composite material comprising a mixture of silane functionalized polyaromatic polymer and an organic or inorganic material containing moieties reactive with the silane groups. In most cases, these treatments result in significant improvements in the ultimate stiffness of the composite. However, one major drawback lies in the fact that, in the presence of the different coupling agents and additives, the chemical bonds formed between hydroxyapatite and the polymer matrix are too "permanent" (i.e., they are too strong and too stable to hydrolysis, dissolution, and/or biological/enzymatic attack) thereby inhibiting the remodeling of the grafting material and gradual degradation of the composite.

SUMMARY OF THE INVENTION

The disadvantages of the prior art are overcome by the present invention, which provides a system for producing composite materials by binding a biocompatible organic polymeric matrix to the mineral portion of bone using coupling agents.

The invention provides composite materials that are useful as bone substitutes for weight-bearing purposes, exhibit improved mechanical properties as a result of enhanced interfacial stability, and, unlike the hydroxyapatite/polymer composites described above, are also able to gradually transfer the initial load to the host bone tissue as they undergo remodeling and degradation.

Natural bone has been shown to be not as structurally close to hydroxyapatite (the chemical formula of which is: $Ca_5(PO_4)_3OH$) as was originally believed. For example, in addition to calcium phosphate, natural bone is also made of carbonate ions, magnesium, sodium, hydrogenophosphate ions and trace elements. There is also evidence that, unlike hydroxyapatite, bone crystals contain only a few hydroxyl groups [Bonar et al. "Structural and composition studies on the mineral of newly formed dental enamel: A chemical, x-ray diffraction, and $^{31}P$ and proton nuclear magnetic resonance study" J. Bone Min. Res. 6:1197-1176 (1991)]. Moreover, many of the carbonate ($CO_3^{2-}$) and hydrogenophosphate ($HPO_4^{2-}$) groups in bone crystals are, from the structural and chemical points of view, unstable and very reactive, thus providing certain physical, chemical and biological functional features important in the formation and dissolution of the crystals in biological tissues. In addition, the short-range environment of the $HPO_4^{2-}$ groups in bone crystals has been shown to be distinctly different from that of the $HPO_4^{2-}$ groups in synthetic apatites and other related calcium phosphate crystals [Wu, Ph. D. thesis MIT, "Solid state NMR study of bone mineral", August 1992]. These differences between bone crystals and synthetic hydroxyapatite result in significant differences in their reactivity, biodegradability and remodeling ability in vivo.

The chemical bonds created between the mineral portion of bone and a polymer are thus weaker and less stable (to hydrolysis, dissolution, and/or biological/enzymatic attack) than those formed between hydroxyapatite and a polymeric matrix. Consequently, in the case of bone-derived composites, the use of coupling agents described in this invention leads to a better interfacial adhesion and therefore to more favorable mechanical properties without causing the problems associated with inhibition of remodeling and biodegradability that arise when hydroxyapatite serves as mineral filler. The fact that the mechanical strength of the bone-polymer composites is improved (only) for the time period required for the bone healing process to be completed constitutes one of the major advantages of the present invention.

The invention also provides preparation methods that allow control over the chemical strength and biological/chemical/enzymatic stability of the bonds formed between the mineral portion of bone and the organic matrix. More specifically, the invention provides strategies for weakening or strengthening the chemical bonds. The stability of these bonds can be reduced by modifying either the mineral phase or the polymeric matrix phase, or both. These modifications, carried out before incorporation of the bone particles into the polymer, make these materials less chemically and biologically stable. One way to modify the bone surface is to recrystallize it in order to generate a more soluble mineral composition. This can be accomplished, for example, by treating the bone surface with dilute phosphoric acid, which substantially transforms the apatite to dicalcium phosphate dihydrate. The modified bone particles end up being coupled to the polymer matrix through the less stable dicalcium phosphate crystals. On the other hand, methods can be used to strengthen the polymer/bone particles bonds by improving the binding of the coupling agent to the polymer matrix. Several strategies exist: the coupling agent can be optimized to efficiently bind to the matrix material used, polymers can be chemically modified and made more reactive to the coupling agent used, or a cross-linking agent can be added to the composite to help the binding of the coupling agent to the polymer. All these methods make it easier to prepare bone-derived composites with controlled, predictable stability and with mechanical properties that can be tailored to meet the needs and requirements of their clinical applications.

In the systems described in this invention, the bone particles can be of autologous, allogenic or xenogenic origin, prepared from cortical bone, cancellous bone, or corticocancellous bone, and can be nondemineralized, deorganified or anorganic. The organic matrices are preferably biocompatible polymers and, if desired, degradable biocompatible polymers. They can be of natural or synthetic origin, or any combination of natural and synthetic polymers. In one embodiment, the coupling agents are silane compounds. The incorporation of bone particles into the polymer matrix can be achieved using one or a combination of fabrication techniques known to those skilled in the art.

Another aspect of the invention concerns composites formed by reacting bone particles with coupling agents before incorporation into a biocompatible organic polymer. The polymeric matrix and/or the surface of the bone particles can be optionally modified beforehand. The final products made using these composites can be formed by molding, casting, machining, vacuum forming, or any fabrication technique or combination of fabrication techniques known in the art. The constructs containing the nondemineralized bone particles are preferentially weight bearing and are able to initially support load and gradually transfer this load to the host bone tissue as it remodels the implants.

In another aspect, the invention provides bone substitute materials that can be used for non load-bearing purposes. For example, a flowable material for filling defects in cancellous bone such as vertebral bodies might benefit from a strong interaction between the bone particles and the fluid or gel phase. This can prevent settling and improve the lubrication and flow properties of the material in order to make injection easier.

Another important advantage of the composites described in this invention lies in their ability to function as a carrier for, and effectively incorporate, one or more medically/surgically useful substances. For example, these substances can promote new bone growth and connective tissue regeneration, and/or accelerate wound healing.

The present invention also provides a method for binding an organic polymeric matrix, through the use of coupling agents, to constructs that incorporate large pieces of bone. For example, the coupling agent can be used to bond a polymeric surface coating to a monolithic bone piece or to bond several columns of bone together to form a weight bearing implant.

DEFINITIONS

The term osteogenic, as used herein, refers to the ability of a substance or material to induce new bone formation via the participation of living cells from within the substance.

The term osteoconductive, as used herein, refers to the ability of a substance or material to provide biologically inert surfaces which are receptive to the growth of new host bone.

The term osteoinductive as used herein, refers to the ability of a substance or material to recruit cells from the host that have the potential for repairing the bone tissue.

The term osteoimplant is herein used in its broadest sense and is not intended to be limited to any particular shapes, sizes, configurations or applications.

Mechanical strength as used herein, refers to those properties exhibited by a bone graft, including loading strength, compressive strength, and tensile strength.

The terms load bearing or weight bearing as used herein, refer to a bone product for implantation in a patient at a site where the bone graft is expected to withstand some level of physical load. The terms "load bearing" and "weight bearing" are herein used interchangeably.

Nondemineralized, as herein applied to bone particles, refers to bone particles that were not subjected to a demineralization process (i.e., a procedure that totally or partially removes the original inorganic content of bone).

Demineralized, as herein applied to bone particles, refers to bone particles that were subjected to a demineralization process (i.e., a procedure that totally or partially removes the original inorganic content of bone).

Deorganified, as herein applied to bone particles, refers to bone particles that were subjected to a process that removes part of their original organic content.

Anorganic, as herein applied to bone particles, refers to bone particles that were subjected to a process that removes their entire original organic content.

The term biocompatible, as used herein, is intended to describe materials that upon administration in vivo, do not induce undesirable long-term effects.

Biodegradable, as used herein, refers to the characteristic that materials will degrade under physiological conditions to form a product that can be metabolized or excreted without damage to organs. Biodegradable materials are not necessarily hydrolytically degradable and may require enzymatic action to fully degrade. Biodegradable materials also include materials that are broken down by or within cells.

The term coupling agent, as used herein, refers to reagents that link the mineral portion of bone to the organic polymeric matrix.

A cross-linking agent, as used herein, is a compound that promotes the formation of a covalent bond between the polymer matrix and the bone particles through a coupling agent.

The term biomolecules, as used herein, refers to the classes of molecules (e.g., proteins, amino acids, peptides, polynucleotides, nucleotides, carbohydrates, sugars, lipids, glycoproteins, nucleoproteins, lipoproteins, steroids, etc) that are commonly found in cells or tissues, whether the molecules themselves are naturally-occurring or artificially created (e.g., by synthetic or recombinant methods). For example, biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

The terms polynucleotide, nucleic acid, and oligonucleotide refer to polymers of nucleotides. These terms can be used interchangeably. Typically, a polynucleotide comprises at least three nucleosides (i.e., adenosine, thymidine, guanosine, cytidine, uridine, deoxyadenosine, deoxythymidine, deoxyguanosine, and deoxycytidine), nucleoside analogs (e.g., 2-amino-adenosine, 2-thiothymidine, inosine, pyrrolopyrimidine, 3-methyl adenosine, C5-pronynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

A polypeptide, peptide or protein comprises a string of at least three amino acids linked together by peptide bonds. The terms "polypeptide", "peptide" and "protein" may be used interchangeably. Peptide may refer to an individual peptide or a collection of peptides. Inventive peptides preferably contain only natural amino acids, although non-natural amino-acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification. In a preferred embodiment, the modifications of the peptide lead to a more stable peptide (e.g., greater half-life in vivo). These modifications may include cyclization of the peptide, the incorporation of D-amino-acids, etc. None of the modifications should substantially interfere with the desired biological activity of the peptide.

The terms polysaccharide, carbohydrate and oligosaccharide refer to a polymer of sugars. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2'-deoxyribose, and hexose). The terms "polysaccharide", "carbohydrate" and "oligosaccharide" may be used interchangeably.

The term small molecule is used to refer to molecules, whether naturally-occurring or artificially created (e.g., via chemical synthesis) that have a relatively low molecular weight. Typically, small molecules are monomeric and have a molecular weight of less than about 1500 g/mol. Preferred small molecules are biologically active in that they produce a local or systemic effect in the patient. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered acceptable for use in accordance to the present invention.

The term bioactive agents, as used herein, refers to compounds or entities that alter, inhibit, activate, or otherwise affect biological or chemical events. For example, bioactive agents include, but are not limited to, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. In certain preferred embodiments, the bioactive agent is a drug.

A more complete listing of bioactive agents and specific drugs suitable for use in the present invention may be found in "Pharmaceutical Substances: Syntheses, Patents, Applications" by Axel Kleemann and Jugen Engel, Thieme Medical Publishing, 1999; the "Merk Index: An Encyclopedia of Chemicals, Drugs, and Biologicals", Edited by Susan Budavri et al., CRC Press, 1996, and the United States Pharmacopeia-25/National Formulary-20, published by the United States Pharmacopeial Convention, Inc., Rockville Md., 2001, all of which are incorporated herein by reference.

A targeting agent, as used herein, is any chemical entity which, when included in an inventive composite, will direct the composite to a particular site or cause the inventive composite to remain in a particular site within the recipient's body. A targeting agent may be a small molecule, peptide, protein, biological molecule, polynucleotide, etc. Typical targeting agents are antibodies, ligands of known receptors, and receptors.

DETAILED DESCRIPTION OF CERTAIN PREFERRED EMBODIMENTS

The present invention provides a bone-polymer composite for use in orthopedic medicine, where it may serve as a bone substitute material, or provide a convenient source of bone-derived particles for producing weight bearing implants. Preferred inventive composites are materials that are biocompatible, display strength throughout the bone repair and remodeling process, and resorb gradually. In particular, the invention provides a composite that is made by bonding a biocompatible polymer to the mineral portion of bone particles using a coupling agent.

Certain aspects of preferred embodiments of the invention are described below in more detail. Those of ordinary skill will appreciate that a variety of embodiments or versions of the invention are not specifically discussed but are nonetheless within the scope of the present invention, as defined by the appended claims.

Bone Particles

The bone particles employed in the preparation of the bone/polymer composite of the invention can be obtained from cortical, cancellous and/or cortico-cancellous bone which may be of autogenous, allogenic and/or xenogenic origin. However, it is preferred that the source of the bone be matched to the eventual recipient of the inventive composition (i.e., the donor and recipient should, at least, be of the same species).

Preparation of Bone Particles.

Methods of preparation of bone particles are known in the art. Bone particles can be formed by milling whole bone to produce fibers, chipping whole bone, cutting whole bone, fracturing whole bone in liquid nitrogen, or otherwise disintegrating the bone tissue. Particles can optionally be sieved to produce those of a specific size. The bone particles employed in the inventive composite can be powdered bone particles possessing a wide range of particles sizes ranging from relatively fine powder to coarse grains and even large chips. In one embodiment, powdered bone particles can range in average particle size from about 0.05 to about 1.2 mm and possess an average median length to median thickness ratio of from about 1:1 to about 3:1. If desired, powdered bone particles can be graded into different sizes to reduce or eliminate any less desirable size(s) of particles that may be present.

Alternatively, or in combination with the aforementioned bone powder, elongate bone particles (that exhibit a high median length to median thickness ratio) can be used. In overall appearance, elongate bone particles can be described as filaments, fibers, threads, slender or narrow strips, etc. Such elongate particles can be obtained by any one of several methods, e.g., by milling or shaving the surface of an entire or relatively large section of bone. Employing a milling technique, one can obtain a mass of elongated bone particles containing, for example, at least about 60 weight percent of elongate bone particles possessing a median length of about 2 to about 200 mm or more, a median thickness of from about 0.05 to about 2 mm, and a median width of from about 1 mm to about 20 mm. Such elongate bone particles can possess a median length to median thickness ratio of at least about 50:1 up to about 500:1 or more, and a median length to median width ratio of from about 10:1 to about 200:1. The milling process may be optimized to adjust the size of the bone particles and the size distribution.

Another procedure for obtaining elongate bone particles, particularly useful for pieces of bone up to about 100 mm in length, is the bone processing mill described in commonly assigned U.S. Pat. No. 5,607,269. Use of this bone mill results in the production of long, thin strips that quickly curl lengthwise to provide tubular-like bone particles. If desired, elongate bone particles can be graded into different sizes to reduce or eliminate any less desirable size(s) that may be present.

The composite of the invention can be made using particulate bone particles, or elongated bone particles or a mixture of both. In the latter case, the mechanical properties of the final composite can be tailored by adjusting the weight percent of the various shapes (elongate or particulate) of bone particles.

Modification of the Components of Bone Particles.

Bone particles used in the fabrication of the inventive composites can be nondemineralized, deorganified or anorganic.

When used in a composite, nondemineralized bone particles play a dual role. They act as a stiffener, providing strength and enhancing the ability to support load, and also bring about new bone ingrowth by osteoinduction. Thus, as the healing process progresses over time, these bone particles are gradually remodeled and replaced by new host bone. The use of nondemineralized bone particles is highly preferred, but not essential, in the fabrication of the composite of the present invention.

Bones particles can be subjected to a process that partially or totally removes their initial organic content to yield deorganified and anorganic bone particles, respectively. Different mineralization methods have been developed and are known to those skilled in the art [Hurley et al. "Anorganic bonechemistry, anatomy, and biological reactions" Milit. Med. 101-104 (1957); Kershaw "Preparation of anorganic bone grafting material" Pharm. J. 8:537 (1963); and U.S. Pat. No. 4,882,149]. The preferred mineralization procedure includes a de-greasing step followed by a basic treatment (with ammonia or an amine) to degrade residual protein and an extensive water washing (U.S. Pat. Nos. 5,417,975 and 5,573,771). Deorganified and anorganic bone particles are used in the composite of the invention when, for example, the presence of organic material residues could lead to undesirable immunological response on implantation.

Other exemplary modifications include removing water, e.g., by drying or lyophilization, and reducing or removing lipids by a defatting process. Defatting may be accomplished using lipase enzymes or washing with a chloroform methanol mixture or by washing in alcohols such as methanol, ethanol or isopropanol. Some form of energy may be provided during washing, for example, through heat, ultrasonic agitation, or application of a pressure gradient. For example, U.S. Pat. No. 5,846,484 discloses methods of using pressure to move fluid from the endosteal portion of bone to the periosteal portion of bone through the vasculature. Essentially, one portion of the bone is placed in a pressure chamber, where fluid is forced into the bone. The fluid passes into the medullary canal and is forced out of the portion of the bone that is outside of the pressure chamber through the vasculature. Application of vacuum allows the process to be run in the reverse direction. One skilled in the art will understand that alternative methods of removing fats or water may also be exploited, including alternative methods of exploiting a pressure gradient to infiltrate bone with a fluid.

Alternatively or in addition, the bone particles may be treated with a detergent, surfactant, or solvent, or pathogens within the bone particles may be removed or inactivated. Exemplary pathogens are well known to those skilled in the art and include bacteria, spores, mold, fungi, and viruses. Methods of removing and/or inactivating these pathogens are well known to those skilled in the art and include for example, radiation sterilization, antibiotic treatment, and treatment with pathogen inactivating chemicals.

Modification of the Surface of Bone Particles.

Optionally, the bone particles used in the preparation of the inventive composite can be modified on their surfaces. In one embodiment, the bone particle surface is chemically treated before being derivatized with a coupling agent. One way to modify the mineral phase is to recrystallize the surface to form a more soluble mineral composition. For example, non-demineralized bone particles may be rinsed with dilute phosphoric acid (e.g., for 1 to 15 minutes in a 5-50% solution by volume). Phosphoric acid reacts with the mineral component of the bone and coats the particles with dicalcium phosphate dihydrate. The latter inorganic compound is more soluble than non-treated bone mineral and therefore forms less stable bonds with the coupling agent.

Coupling Agents

One factor that determines the final performance of a composite material is the quality of the filler/polymer interface. In recent years, the reinforcing power of mineral fillers has been improved by a chemical treatment that links the two components of a composite by covalent bonds using coupling agents. Commonly used coupling agents include silanes, zirconates, and titanates. A wide variety of these coupling agents are commercially available from different manufacturers.

Silane Coupling Agents.

In a preferred embodiment, silane coupling agents are employed to act as mediators and bind a biocompatible organic polymer to the mineral portion of bone particles.

An organosilane molecule has the general chemical formula:

$$R_n SiR'_m$$

where m is a whole number between 1 and (4-n). A silane coupling agent exhibits three main constituents: a silicon atom (Si), which is attached to R, a non hydrolyzable organic functional group (e.g., vinyl, epoxy, amino, methacryl, acryl, isocyanato, thiocyanato, mercapto, chloro, etc) and to R' a hydrolyzable or good leaving functional group (e.g., acetoxy, alkoxy, chloro, hydride, etc). The R' group is involved in the reaction with the inorganic material (mineral filler), while R possesses a functionality which enables the coupling agent to bind covalently to an organic substance (polymeric matrix). Most of the widely used silanes have one organic substituent (i.e., n=1). In most cases, the silane is subjected to hydrolysis prior to the coupling reaction. The highly reactive silanol groups, that are generated by hydrolysis, subsequently form metal hydroxyde or silaxone bonds with the inorganic material. Regardless of the value of m (i.e., m=1, 2 or 3 if n=1), there is usually only one bond formed between the silane and the mineral substrate; the other silanol groups (if present, i.e., if m=2 or 3) exist as either bonded to the silicon atoms of other coupling molecules or in free forms.

Exemplary silanes include: 3-methacryloxypropyltrimethoxysilane, 3-aminopropyltrimethoxysilane, 3-aminopropyltriethoxysilane, 3-glycidoxypropyltrimethoxysilane, trimethoxyvinylsilane, and poly(vinylmethoxysiloxane)

Selection of a Silane Coupling Agent.

Selection of the appropriate coupling agent is accomplished by empirical evaluation of silanes within predicted categories. Exact prediction of the best silane can be complicated as an increase in interfacial adhesion via the use of silanes is the result of a complex series of factors (such as surface energy, polar adsorption, acid-base interaction, etc). Strategies for optimization must take into account the materials on both sides of the interface (i.e., the mineral portion of bone particles and the organic polymer matrix) and their susceptibilities to the various coupling factors.

The number of R' groups on the silane is another important parameter in controlling bond characteristics. The traditional silane coupling agents contain three hydrolyzable or leaving groups (i.e., m=3). These coupling molecules have maximum hydrolytic stability but tend to be hydroscopic. Silanes with two R' groups form less rigid interfaces whereas silanes with only one leaving group yield the most hydrophobic interfaces but have the lowest hydrolytic stability.

In the silane molecule, the silicon atom and the functional group R can be connected by an elongated tether group. Once the silane is attached to the mineral portion of the bone, the tether acts as a spacer between the bone particle and the terminal active group at the other end of the silane molecule. The presence of this tether, which creates some physical distance and thereby reduces steric hindrance, helps make the active R group more accessible to the polymer.

Coupling Reaction.

The coupling reaction can be carried out using different methods known in the art: deposition from aqueous alcohol and deposition from aqueous solutions are the procedures most commonly used for preparing silylated surfaces, whereas bulk deposition onto powders, and integral blend methods, are processes that are more useful in the formulation of composites.

Modification of Silane Coupling Agents.

When the commercially available silane coupling agents do not bear appropriate terminal functional groups that match, at one end, the chemical reactivity of the mineral portion of bone and, at the other end, the chemical reactivity of the organic polymer matrix, the silane molecule can be modified. Once the coupling agent is attached to the bone particles, its R functional group can be submitted to a large number of chemical reactions. These chemical modifications can also be carried out before reaction between the silane and the bone particles. One skilled in the art will readily recognize how to modify R groups such as amino, alkoxy, ketones, aromatic moieties, etc.

In addition, the silane can be used to attach a biologically active compound, such as a biomolecule, a small molecule or a bioactive agent, to the bone particles before their incorporation into the polymeric matrix (as described below). The silane can be optimized for the specific compound to be associated with the bone particles. In one embodiment, the composite of the invention can be made using silanes bearing different terminal groups R with functionalities to match the chemical reactivity of the organic polymeric matrix and that of the different biologically active compounds to be incorporated into the composite. Similarly, non biologically active substances can be attached to the bone particles through the silane coupling agent (see below).

Cross-Linking Agents.

Another way to favor the formation of a covalent bond between the silane molecule and the organic polymer matrix is to use cross-linking agents. A large number of chemical cross-linking agents are known to those skilled in the art. In a preferred embodiment, the cross-linkers used in the preparation of the inventive composites are biocompatible heterobifunctional molecules.

A wide variety of heterobifuntional cross-linkers are known in the art. These include, but are not limited to, N-hydroxysuccinimide derivatives and their water soluble analogs: N-hydroxysulfosuccinimide derivatives, carbodiimide derivatives, as well as derivatives of aldehydes, epoxy compounds, polyvalent metallic oxides, organic tannins, maleimides, sulfides, phenolic oxides, hydrazide, isocyanates, thioisocyanates, etc.

Polymers

Suitable polymers useful for the preparation of the inventive composites are preferably biocompatible polymers, that can be of natural or synthetic origin or a combination of natural and synthetic polymers.

Natural polymers include polysaccharides and proteins. Exemplary polysaccharides include starches, dextrans, and celluloses; exemplary proteins include collagen and gelatin. Polysaccharides such as starches, dextrans, and celluloses may be unmodified or may be modified physically or chemically to affect one or more of their properties such as their characteristics in the hydrated state, their solubility, or their half-life in vivo. An exemplary modified polysaccharide is ethyl cellulose.

In one embodiment, the organic matrices are biocompatible, degradable polymers. These polymers can be broken down by cellular action or/and by action of non-living body fluid components. A variety of biocompatible, degradable polymers can be used. These include, but are not limited to, polyanhydrides, polyesters, polyorthoesters, poly(propylene fumerates), polyglyconates, poly(hydroxy acids), polyphosphazenes, biodegradable polycyanoacrylates, polycaprolactones, poly(vinyl pyrrolidones), polyamides, polyurethanes, polyesteramides, polydioxanones, polyacetals, polyketals, polycarbonates, polysulfones, polyorthocarbonates, polyhydroxybutyrates (e.g., poly(3-hydroxybutyric acid)), polyhydroxyvalerates, polyalkylene oxalates, polyalkylene succinates, poly(maleic acid), poly(amino acids), poly(methyl vinyl ether), poly(maleic anhydride), tyrosine based polymers, including but not limited to polycarbonates and polyarylates (Pulapura, et al., *Biopolymers*, 1992, 32: 411-417; and Hooper, et al., *J. Bioactive and Compatible Polymers*, 1995, 10:327-340), Polysorb™ (available from Igus Inc., Providence, R.I.), chitin, chitosan, and copolymers, terpolymers, or higher poly-monomer polymers thereof or combinations or mixtures thereof. Examples include poly(glycolide lactide-co-lactide), starch ethylene vinyl alcohol, poly(3-hydroxybutyric acid-co-3-hydroxy-valeric acid), and starch cellulose acetate. Non-biodegradable polymers may also be used as well. For example, polypyrrole, polyanilines, polythiophene, and derivatives thereof are useful electroactive polymers that can transmit voltage from the endogenous bone to an implant. Other non-biodegradable, yet biocompatible polymers include polystyrene, non-biodegradable polyurethanes, polyureas, poly(ethylene vinyl acetate), polypropylene, polymethacrylate, polyethylene, and poly(ethylene oxide). Copolymers, mixtures, and adducts of the above polymers may also be used with the invention.

In one embodiment, polyhydroxy acids such as polylactic acid (PLA), polyglycolic acid (PGA), and their copolymers (PLGA), (e.g., poly(lactide-co-glycolide); 75/25), are used. These are among the synthetic polymers approved for human clinical use as surgical suture materials and in controlled release devices. They are degraded by hydrolysis to products that can be metabolized and excreted. Furthermore, copolymerization of PLA and PGA offers the advantage of a large spectrum of degradation rates from a few days to several years by simply varying the copolymer ratio of glycolic acid to lactic acid (which is more hydrophobic and less crystalline than PGA and degrades at a slower rate). In addition, the optical activity of poly(lactic acid) may be manipulated to control the degradation rate and other properties of the polymer. For example, poly(L-lactide) may be used alone or in a copolymer or mixture with poly(D,L-lactide), e.g., poly(L-lactide-co-D,L-lactide). Exemplary ratios of L-lactide to D,L-lactide include 70/30.

In some embodiments, the biocompatible polymer may not be a polyaromatic polymer.

Methods for using these polymers are well known. In general, the polymers are dissolved in an organic solvent such as methylene chloride or chloroform to mix with a mineral filler. The amount of solvent has only a minimal effect on the structure of the produced materials, but affects the solvent evaporation time. Preferably, the solvent contains a chlorine molecule, such as, for example, the solvents chloroform and methylene chloride. The preferred solvent is chloroform.

Preparation of the Composite and Composite Processing

The composites of the invention may be reacted and then formed into the desired shape or first formed or molded and then reacted into a fully cured state. Reaction may be achieved by thermal heating, electromagnetic heating or any other suitable means in the presence or absence of catalysts. The incorporation of the bone particles into the polymer matrix can be performed using one (or a combination) of the fabrication techniques known to those skilled in the art, such as solvent casting, melting, etc. The shaping of the inventive composites can be carried out by any one of the following processes: compression molding, transfer molding, extrusion, injection molding, reaction injection molding, sandwich molding, blow molding, extrusion blow molding, injection blow molding, rotational molding, thermoforming, vacuum forming, machining, calendering, slush molding, lamination, spinning, etc.

Exemplary shapes include, but are not limited to, a sheet, plate, particle, sphere, strand, coiled strand, capillary network, film, fiber, mesh, disk, cone, rod, cup, pin, screw, tube, tooth, tooth root, bone or portion of bone, wedge or portion of wedge, cylinder, and threaded cylinder, In one embodiment, the composite is molded into the shape of a desired implant. For example, the mold may be shaped as a portion of a bone or as a whole bone to be replaced. Bones that may be replaced using the composites of the invention include ethmoid, frontal, nasal occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones. In one embodiment, the composite is molded as a plate or similar support, including but not limited to an I-shape to be placed between teeth for intra-bony defects, a crescent apron for single site use, a rectangular bib for defects including both the buccal and lingual alveolar ridges, neutralization plates, spoon plates, condylar plates, clover leaf plates, compression plates, bridge plates, wave plates, etc. Partial tubular as well as flat composite may be a block that is machined into a desired shape.

In another embodiment, a block of the composite material may be shaved, milled or ground, and the composite particles thus obtained may be combined in a mold having the desired shape or configuration, and pressed to form a solid as described in U.S. Pat. No. 6,294,187. The composite particles may be mixed with additional biocompatible components, including biocompatible binders, fillers, fibers, plasticizers, biostatic/biocidal agents, surface active agents (e.g., surfactants), biomolecules, small molecules, bioactive agents, etc, prior to, during, or after compression of the composite particles.

Wet-laying as described in U.S. Pat. No. 5,507,813 may also be used to assemble and form an implant from the particles of the inventive composite. In this technique, the composite particles are slurried in a suitable liquid and cast in a form such as a flat sheet, mesh screen, or a three-dimensional mold. The wet-laid mass is then dried by removing the liquid by vacuum or evaporation. This process results in particle entanglement that provides the final implant with the ability to retain its shape. Further adhesion between the composite particles may be achieved by including an adhesive in the liquid or by using ultrasonic bonding. Additionally, the liquid may include biocompatible components.

In an alternative embodiment, the completed composite of the invention is melted and molded into a desired shape. Thermoplastic polymers will flow upon heating and may be reshaped without machining. The polymer may be rolled or extruded to form a particular shape or molded in the shape of a desired implant, as discussed above. In an alternative embodiment, the composite is at least partially melted and inserted into an implant site before cooling.

Incorporation of Other Materials Including Biologically-Active Agent

The composites of the invention are useful as stand alone materials, but they can also be combined with other substrate materials to modify their properties. Thus, an important advantage of the inventive composites lies in their ability to function as a carrier for, and effectively incorporate, one or more useful substances. These substances can be biologically active or non biologically active compounds.

Biologically Active Substances.

In one embodiment, the substances incorporated into the composite of the invention promote new bone growth and connective tissue generation and/or accelerate wound healing (see, for example, U.S. Pat. No. 5,073,114). Examples of materials that can be incorporated include antibiotics, chemotherapeutics and bone cell inducers and stimulators, including the general class of cytokines such as the TGF-β superfamily of bone growth factors ["Cytokines and Bone Metabolism" Gowen, ed, CRC press (1992)], the family of bone morphogenetic proteins, osteoinductors, and/or bone marrow or bone forming precursor cells, isolated using standard techniques. Sources and amounts of various materials that can be included are known to those skilled in the art [Glowacki et al. "The role of osteocalcin in osteoclast differentiation" J. Cellular Biochem. 45:292-302 (1991); Ballock et al. "Regulation of collagen expression in periosteal cells by three members of the TGF-β superfamily" Thirty Ninth Annual Meeting, Orthopaedic Research Society; 18,734 (1993); Ripamonti et al. "Induction of bone in composites of osteogenin and porous hydroxyapatite in baboons" J. Plastic and Reconstructive Surg. 89:731-739 (1991); Ripamonti et al. "Growth and morphogenetic factors in bone induction: role of osteogenin and related bone morphogenetic proteins"

CRC Critical Reviews in Oral Biol. Med. 3:1-14 (1992); Ripamonti et al. "Initiation of bone regeneration in baboons by osteogenin, a bone morphogenetic protein" Matrix; 12:40-55 (1992); Ripamonti et al. "Xenogeneic osteogenin and demineralized bone matrices including human induced bone differentiation in athymic rats and baboons" Matrix 11:404-411 (1991); Cook et al. "Restoration or large diaphyseal segmental defects in rabbits using recombinant human osteogenic protein (OP-1)" Combined meetings of Orthopaedic Research societies of USA, Japan and Canada 1, 66 (1991); Miyamoto et al. "Trans-filter bone induction in monkeys by bone morphogenetic protein" Thirty Ninth Annual Meeting, Orthopaedic Research Society 18, 99 (1993); Yasko et al. "Comparison of recombinant human BMP-2 versus cancellous bone to heal segmental bone defects" Thirty Ninth Annual Meeting, Orthopaedic Research Society 18, 100 (1993); Aspenberg et al. "Bone morphogenetic protein induces bone in the squirrel monkey, but bone matrix does not" Thirty Ninth Annual Meeting, Orthopaedic Research Society 18, 101 (1993); Iwasaki et al. "Bone morphogenetic protein-2 stimulates osteogenesis in high density culture of periosteum-derived cells" Thirty Ninth Annual Meeting, Orthopaedic Research Society 18, 483 (1993); Cook et al. "Recombinant human osteogenic protein-1 (rhOP-1) heals segmental long-bone defects in non-human primates" Thirty Ninth Annual Meeting, Orthopaedic Research Society 18, 484 (1993); and Hunt et al. "Healing of a segmental defect in the rat femur using a bone inducing agent (BIA) derived from a cultured human osteosarcoma cell line (SAOS-2)" Thirty Ninth Annual Meeting, Orthopaedic Research Society 18, 489 (1993)].

To enhance biodegradation in vivo, the composites of the present invention can also include different enzymes. Preferred enzymes or similar reagents are proteases or hydrolases with ester-hydrolyzing capabilities. Such enzymes include, but are not limited to, proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase, an oxidase or the like. The inclusion of an appropriate amount of such a degradation enhancing agent can be used to regulate implant duration.

Suitable biologically-active agents also include substances useful in preventing infection at the implant site, as for example, antiviral, antibacterial, antiparasitic, antifungal substances and combinations thereof. The agent may further be a substance capable of acting as a stimulant, sedative, hypnotic, analgesic, anticonvulsant, and the like. Anti-inflammatory compounds embedded within the composite will control the cellular response long after the initial response to implantation of the composite.

Inventive compositions may alternatively or additionally be used to deliver other pharmaceutical agents including antibiotics, anti-neoplastic agents, growth factors, hematopoietic factors, nutrients, etc. Bioactive agents that can be delivered using the inventive composites include non-collagenous proteins such as osteopontin, osteonectin, bone sialo proteins, fibronectin, laminin, fibrinogen, vitronectin, trombospondin, proteoglycans, decorin, proteoglycans, beta-glycan, biglycan, aggrecan, veriscan, tanascin, matrix gla protein hyaluran, cells; amino acids; peptides; inorganic elements; inorganic compounds; organometallic compounds; cofactors for protein synthesis; cofactors for enzymes; vitamins; hormones; soluble and insoluble components of the immune system; soluble and insoluble receptors including truncated forms; soluble, insoluble, and cell surface bound ligands including truncated forms; chemokines, interleukines; antigens; bioactive compounds that are endocytosed; tissue or tissue fragments; endocrine tissue; enzymes such as collagenase, peptidases, oxidases, etc; polymeric cell scaffolds with parenchymal cells; angiogenic drugs, polymeric carriers containing bioactive agents; encapsulated bioactive agents; bioactive agents in time-release form; collagen lattices, antigenic agents; cytoskeletal agents; cartilage fragments; living cells such as chondrocytes, osteoblasts, osteoclasts, fibroclasts, bone marrow cells, mesenchymal stem cells, etc; tissue transplants; bioadhesives; bone morphogenic proteins (BMPs), transforming growth factors (TGF-beta), insulin-like growth factor (IGF-1, IGF-2), platelet derived growth factor (PDGF); fibroblast growth factors (FGF), vascular endothelial growth factors (VEGF), epidermal growth factor (EGF), growth factor binding proteins, e.g., insulin-like growth factors (IGFBP-2, IGFBP-3, IGFBP-4, IGFBP-5, IGFBP-6); angiogenic agents; bone promoters; cytokines; interleukins; genetic material; genes encoding bone promoting action; cells containing genes encoding bone promoting action; cells genetically altered by the hand of man; externally expanded autograft or xenograft cells; growth hormones such as somatotropin; bone digestors; anti-tumor agents; fibronectin; cellular attractants and attachment agents; immunosuppressants; bone resorption inhibitors and stimulators; mitogenic factors; bioactive factors that inhibit and stimulate second messenger molecules; cell adhesion molecules, e.g., cell-matrix and cell-cell adhesion molecules; secondary messengers; monoclonal antibodies specific to cell surface determinants on mesenchymal stem cells; portions of monoclonal antibodies specific to cell surface determinants on mesenchymal stem cells; portions of monoconal antibodies specific to cell surface determinants on mesenchymal stem cells; clotting factors; polynucleotides; and combinations thereof. The amount of the bioactive agent included in the composite can vary widely and will depend on such factors as the agent being delivered, the site of administration, the patient's physiological condition, etc. The optimum levels will be determined in a specific case based upon the intended use of the implant.

For example, inventive composites may be prepared so that they include one or more compounds selected from the group consisting of drugs that act at synaptic and neuroeffector junctional sites (e.g., acetylcholine, methacholine, pilocarpine, atropine, scopolamine, physostigmine, succinylcholine, epinephrine, norepinephrin, dopamine, dobutamine, isoproterenol, albuterol, propanolol, serotonin); drugs that can act on the central nervous system (e.g., clonazepam, diazepam, lorazepam, benzocaine, bupivacaine, lidocaine, tetracaine, ropivacaine, amitriptyline, fluoxetine, paroxetine, valproic acid, carbamazepine, bromocriptine, morphine, fentanyl, naltrexone, naloxone); drugs that can modulate inflammatory responses (e.g., aspirin, indomethacin, ibuprofen, naproxen, steroids, cromolyn sodium, theophylline); drugs that affect renal and/or cardiovascular functions (e.g., furosemide, thiazide, amiloride, spironolactone, captopril, enalapril, lisinopril, diltiazem, nifedipine, verapamil, digoxin, isordil, dobutamine, lidocaine, quinidine, adenosine, digitalis, mevastatin, lovastatin, simvastatin, mevalonate); drugs that affect gastrointestinal function (e.g., omeprazole, sucralfate); antibiotics (e.g., tetracycline. clindamycin, amphotericin B, quinine, methicillin, vancomycin, penicillin G, amoxicillin, gentamicin, erythomycin, ciprofloxacin, doxycycline, acyclovir, zidovudine (AZT), ddC, ddI, ribavirin, cefaclor, cephalexin, streptomycin, gentamicin, tobramycin, chloramphenicol, isoniazid, fluconazole, amantadine, interferon); anti-cancer agents (e.g., cyclophosphamide, methotrexate, fluorouracil, cytarabine, mercaptopurine, vinblastine, vincristine, doxorubicin, bleomycin, mitomycin C, hydroxyurea, prednisone, tamoxifen, cisplatin, decarbazine); immunomodulatory agents (e.g., interleukins, interferons, GM-CSF, TNF-β, cyclosporin, FK506, azathioprine, steroids); drugs acting on the blood and/or the blood-forming organs (e.g., interleukins, G-CSF, GM-CSF, erythropoietin, vitamins, iron, copper, vitamin $B_{12}$, folic acid, heparin, warfarin, coumarin); hormones (e.g., growth hormone (GH), prolactin, luteinizing hormone, TSH, ACTH, insulin, FSH, CG, somatostatin, estrogens, androgens, progesterone, gonadotropin-releasing hormone (GnRH), thyroxine, triidothyronine); hormone antagonists; agents affecting calcification and bone turnover (e.g., calcium, phosphate, parathyroid hormone (PTH), vitamin D, bisphosphonates, calcitonin, fluoride); vitamins (e.g., riboflavin, nicotinic acid, pyridoxine, pantothenic acid, biotin, choline, inositol, carnitine, vitamin C, vitamin A, vitamin E, vitamin K); gene therapy agents (e.g., viral vectors, nucleic-acid-bearing liposomes, DNA-protein conjugates, anti-sense agents); or other agents such as targeting agents, etc.

Non Biologically Active Agents.

Non biologically active materials may also be incorporated into the inventive composites. For example, radiopaque (see, for example, U.S. Pat. No. 5,676,146), luminescent, or magnetically active particles may be used. As the bone is resorbed, these non-biodegradable materials are removed from the tissue site by natural metabolic processes, allowing the degradation of the polymer and the resorption of the bone particles to be tracked using standard medical diagnostic techniques. The composites of this invention may further contain other materials such as fillers to improve the strength of the polymer matrices, anti-degradants such as anti-oxidants and anti-ozonants, colorants, chromophores or any other material that may alter or change the property of the composites.

Incorporation of Other Materials.

In certain embodiments, the agent to be delivered is adsorbed to or otherwise associated with the composite. The agent may be associated with the composite through specific or non-specific interactions; or covalent or non-covalent interactions. Examples of specific interactions include those between a ligand and a receptor, an epitope, and an antibody, etc. Examples of non-specific interactions include hydrophobic interactions, electrostatic interactions, magnetic interactions, dipole interactions, van der Waals interactions, hydrogen bonding, etc.

Generally, the substances to be added to the composite can be chemically or physically bond to the polymer matrix or to the bone particles before formation of the composite. In that case, the agents to be added are preferably either insoluble or substantially insoluble in the leaching media. As discussed above, biologically active and non-biologically active compounds can be linked to the bone particles through the silane coupling agents. The substances can also be added after formation of the composite by standard dip or spray application techniques followed by drying. Alternatively, after removal of the pore-forming agent, the composite can be treated with reagents that generate functional groups in the polymeric matrix to which biologically active or non biologically active agents can be chemically or physically attached. In certain embodiments, the agent is attached to the matrix using a linker so that the agent is free to associate with its receptor or site of action in vivo. In certain preferred embodiments, the agent to be delivered may be attached to a chemical compound such as a peptide that is recognized by the matrix of the composite. In another embodiment, the agent to be delivered is attached to an antibody, or fragment thereof, that recognizes an epitope found within the matrix of the composite. In a preferred embodiment, the agent is BMP, TGF-β, IGF, parathyroid hormone (PTH), growth factors, or angiogenic factors. In certain embodiments, at least two bioactive agents are attached to the composite. In other embodiments, at least three bioactive agents are attached to the composite.

Preferably, the site, where the biologically active or non biologically active agents are attached to in the composite, are biodegradable so that the agents can be released to the adjacent tissue fluids during biodegradation of the matrix. Preferably, agents are released into the surrounding tissue fluids at a controlled rate. For example, the polymer matrix may be formulated to degrade after an effective and/or substantial amount of the agent is released from the matrix. Release of a substance having a low solubility in water, as for example, a peptide or protein, may require the degradation of a substantial part of the polymer matrix to expose the agent directly to the surrounding tissue fluids. Thus, the release of the agent from the matrix may be varied by, for example, the solubility of the agent in water, the distribution of the agent within the matrix, or the size, shape, porosity, solubility and biodegradability of the polymer matrix.

Treatments of the Implant

Once the composite of the invention has been shaped into an implant, it can be used as such or further processed. The goal of these further treatments is to modify the properties of the implant, such as its rate of degradation or its ability to promote bone growth, and/or to change the shape of the implant in order to broaden the range of its potential clinical applications.

For example the surface of the implant can be oxidized using a solvent or gas to break some of the polymer chains and thereby accelerate the initial decomposition of the implant. The surface of the implant can also be roughened to promote bony on-growth. This can be achieved by sanding, filing, plasma etching, chemically etching, or mechanically pitting. Different procedures aimed at attaching biologically active and non biologically active compounds to the inventive implants have been described above. In addition to these procedures, the surface of the composite can be submitted to plasma etching or chemical oxidation to render the implant more reactive and increase its affinity for the agent to be attached to it (see U.S. Pat. Nos. 6,033,582 and 6,119,028).

The implant can also be machined according to techniques well known in the art. For example, holes may be drilled to facilitate bony ingrowth or to provide channels for suturing tissues to the implant. Alternatively, a composite shaped as a block can be machined into a desired shape. These machined components may be attached to one another using mechanical fasteners such as dowels, pins, and screws, all of which may be fabricated from the composite of the invention. Traditional joints such as tongue-and-groove or mortoise-and-tenon may be employed as the machined pieces are assembled.

Alternatively, or in addition, the machined pieces may be attached to one another, by using a biocompatible adhesive or a chemical cross-linking agent or by ultrasonic bonding. Biocompatible adhesives include, but are not limited to, biocompatible cyanoacrylates, epoxy-based compounds, dental resin sealants, dental resin cements, glass ionomer cements, poly (methyl methacrylate), gelatin-resorcinol-formaldehyde glues, collagen-based glues, inorganic bonding agents such as zinc phosphate, magnesium phosphate, and other phosphate based cements, zinc carboxylate, and protein-based binders, such as fibrin glues and mussel-derived adhesive proteins.

Additional Applications

Non Weight Bearing Applications.

In another embodiment, the invention provides bone substitute materials that can be used for non load bearing purposes. For example, a flowable material for filling defects in cancellous bone such as vertebral bodies might benefit from a strong interaction between the bone particles and the fluid or gel phase. This can prevent settling and improve the lubrication and flow properties of the material in order to make injection easier. Depending on the composition of the fluid or gel phase and the nature of the R group on the silane, the interaction may be direct or indirect covalent or non-covalent interaction. Desirable non-covalent interactions include hydrogen bonding, van der Waals interactions, hydrophobic interactions, electrostatic interactions, etc.

Other Preparation Methods.

In addition to bone particles, the methods of the invention can be applied to constructs that incorporate large pieces of bone. A coupling agent can be used to bind a polymeric surface coating to a monolithic bone piece.

Several methods are known in the art to bond machined composite pieces to one another, these include, for example, application of known and conventional biologically compatible adhesives or addition of biocompatible chemical cross-linking agents, use of mechanical fasteners, which can be fabricated from natural and synthetic materials and bioabsorbable as well as nonbioabsorbable materials, laser tissue welding, and, ultrasonic bonding. The inventive method provides a new way to efficiently bond columns of bone and bone-derived composite together to form a weight bearing implant.

As described in U.S. Pat. No. 5,899,939, the final bone-derived implant can optionally possess one or more layers formed from one or more other materials. For example, these optional layers can be based on or include highly or fully demineralized bone, graphite or pyrolytic carbon, a mineral material such as hydroxyapatite, tricalcium phosphate, bioglass or other bioceramic, or natural or synthetic polymers.

What is claimed is:

1. A method for producing a bone-polymer composite comprising: (a) providing a plurality of bone particles; (b) treating the bone particles with a silane coupling agent such that the silane coupling agent is directly coupled to the bone particles; and (c) incorporating the bone particles obtained from (b) into a polymer, wherein the polymer is not a polyaromatic polymer.

2. The method of claim 1, wherein the bone particles are obtained from one or more of autologous bone, allogenic bone, xenogenic bone, and mixtures thereof.

3. The method of claim 1, wherein the bone particles are obtained from one or more of cortical bone, cancellous bone, cortico-cancellous bone, and mixtures thereof.

4. The method of claim 1, wherein the bone particles are obtained from one or more of nondemineralized bone, deorganified bone, anorganic bone, and mixtures thereof.

5. The method of claim 1, wherein the coupling agent is a silane selected from the group consisting of silanes bearing one hydrolyzable or leaving group, silanes bearing two hydrolyzable or leaving groups, and silanes bearing three hydrolyzable or leaving groups.

6. The method of claim 1, wherein the polymer is a biocompatible polymer selected from the group consisting of polymers of natural origin, polymers of artificial origin, and any combination of natural and artificial polymers.

7. The method of claim 1, wherein the polymer is selected from the group consisting of biodegradable polymers, non-biodegradable polymers, co-polymers of biodegradable polymers, co-polymers of non-biodegradable polymers, and co-polymers of biodegradable and non-biodegradable polymers.

8. The method of claim 1, wherein the polymer is a natural polymer selected from the group consisting of polysaccharides and proteins.

9. The method of claim 8, wherein the polymer is selected from the group consisting of starch, dextran, cellulose, gelatin, and collagen.

10. The method of claim 1, wherein the polymer is an artificial polymer selected from the group consisting of poly(anhydrides), poly(hydroxy acids), polyesters, poly(orthoesters), polycarbonates, poly(propylene fumerates), poly(caprolactones), polyamides, polyamino acids, polyacetals, polylactides, polyglycolides, polysulfones, poly(dioxanones), polyhydroxybutyrates, polyhydroxyvalyrates, poly(vinyl pyrrolidones), biodegradable polycyanoacrylates, biodegradable polyurethanes, polysaccharides, tyrosine-based polymers, poly(methyl vinyl ether), poly(maleic anhydride), poly(glyconates), polyphosphazines, poly(esteramides), polyketals, poly(orthocarbonates), poly(maleic acid), poly(alkylene oxalates), poly(alkylene succinates), nonbiodegradable polyurethanes, polyureas, poly(ethylene vinyl acetate), polypropylene, polymethacrylate, polyethylene, poly(ethylene oxide), and co-polymers, adducts, and mixtures thereof.

11. The method of claim 5, wherein the silane coupling agent attached to the bone particles is linked to the polymer by a member of covalent and non-covalent interactions.

12. The method of claim 1, further comprising the step of modifying a surface of at least a portion of the bone particles before treatment with the coupling agent.

13. The method of claim 12, wherein modifying comprises treating the bone particles with dilute phosphoric acid.

14. The method of claim 1, further comprising the step of modifying a composition of the bone particles before treatment with the coupling agent.

15. The method of claim 14, wherein modifying comprises one or more of drying the bone particles, lyophilizing the bone particles, defatting the bone particles, treating the bone particles with a detergent, treating the bone particles with a solvent, treating the bone particles with a surfactant, removing pathogens, and inactivating pathogens.

16. The method of claim 15, wherein removing pathogens comprises one or more of radiation sterilization, antibiotic treatment, and treatment with a pathogen-inactivating chemical.

17. The method of claim 15, wherein inactivating pathogens comprises one or more of radiation sterilization, antibiotic treatment, and treatment with a pathogen inactivating chemical.

18. The method of claim 1, wherein step (c) further includes combining a cross-linking agent with treated bone particles and the polymer.

19. The method of claim 18, wherein the cross-linking agent is selected from the group consisting of aldehydes, polyepoxy compounds, polyvalent metallic oxides, organic tannins, N-hydroxysuccinimides, N-hydroxysulfosuccinimides, phenolic oxides, hydrazides, carbodiimides, isocyanates, isothiocyanates, sugars, and enzymes.

20. The method of claim 1, wherein step (c) comprises solvent casting, melting, or both.

21. The method of claim 1, further comprising combining the composite with one or more of a wetting agent, biocompatible binder, filler, fiber, plasticizer, biostatic/biocidal agent, surface active agent, biomolecule, small molecule, and bioactive agent.

22. The method of claim 21, wherein the biologically active agent is selected from the group consisting of antibiotics, chemotherapeutics, bone cell inducers, and bone cell stimulators.

23. The method of claim 1, further comprising incorporating osteoblasts into the composite.

24. The method of claim 1, further comprising processing the composite to obtain an osteoimplant having a desired shape.

25. The method of claim 1, wherein the silane coupling agent has a formula:

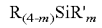

wherein R is a non hydrolyzable organic functional group; R' is a hydrolyzable or good leaving functional group; and m is an integer from 1 to 3.

26. A method for producing a bone-polymer composite comprising: (a) providing a plurality of bone particles; (b) treating the bone particles with a silane coupling agent such that the silane coupling agent is directly coupled to the bone particles; and (c) incorporating the bone particles obtained from (b) into a polymer; wherein the polymer is not a polyaromatic polymer, and wherein the polymer is an artificial polymer selected from the group consisting of poly(caprolactones), polylactides, polyglycolides, biodegradable polyurethanes, nonbiodegradable polyurethanes, and co-polymers, adducts, and mixtures thereof.

27. A method for producing a bone-polymer composite comprising: (a) providing a plurality of bone particles; (b) treating the bone particles with a silane coupling agent such that the silane coupling agent is directly coupled to the bone particles; and (c) incorporating the bone particles obtained from (b) into a polymer, wherein the polymer is not a polyaromatic polymer, and wherein the bone particles represent about 60% to about 75% of the total weight of the composite.

* * * * *